United States Patent [19]

Armstrong et al.

[11] Patent Number: 5,149,715
[45] Date of Patent: Sep. 22, 1992

[54] CONTROL OF FUNGAL DISEASES IN THE PRODUCTION OF MUSHROOMS

[75] Inventors: Gale L. Armstrong, San Mateo; Nigel S. Dunn-Coleman, Los Gatos; Mark Wach, Aptos, all of Calif.

[73] Assignee: Monterey Mushroom, Inc., Capitola, Calif.

[21] Appl. No.: 308,690

[22] Filed: Feb. 9, 1989

[51] Int. Cl.$^5$ ............................................. A01N 35/00
[52] U.S. Cl. ..................................................... 514/701
[58] Field of Search ......................................... 514/701

[56] References Cited

U.S. PATENT DOCUMENTS

| | | | |
|---|---|---|---|
| 4,402,950 | 9/1980 | Wolf et al. | 424/195 |
| 4,477,361 | 2/1983 | Sperti et al. | 252/106 |
| 4,978,686 | 12/1990 | Sotome | 514/701 |

FOREIGN PATENT DOCUMENTS

| | | |
|---|---|---|
| 0133028 | 2/1985 | European Pat. Off. |
| 0142276 | 5/1985 | European Pat. Off. |
| 49-018640 | 2/1974 | Japan |
| 59-044396 | 3/1984 | Japan |
| 59-063182 | 4/1984 | Japan |

OTHER PUBLICATIONS

Kurita, N., et al., "Antifungal activity of components of essential oils" *Agr. and Biol. Chemistry* 45: 945–952 (1981).

Angmor et al., *Journal of Medicinal Plant Research* (1979) 35:342–347.
Bullerman et al., *Journal of Food Science* (1977) 42:1107–1109.
El-Obeid et al., *Pharmazie* (1984) 39(11):778–779.
D. P. Thompson, *Mycologia* (1989) 81(1):151–153.
Mukherjee in *Journal of Plant Diseases and Protection* (1976) 83(6):305–308.

*Primary Examiner*—Allen J. Robinson
*Attorney, Agent, or Firm*—Cooley, Godward, Castro, Huddleson & Tatum

[57] ABSTRACT

A method of controlling toxic fungal diseases in mushrooms is provided which comprises adding an effective fungal-disease-inhibiting amount of a compound of the formula

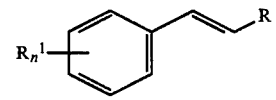

to a substrate in which mushrooms are growing or are to be grown, wherein R represents —$CH_2OH$ or —CHO; n is an integer from 0 to 3; and each $R^1$ independently represents halogen, OH, $NH_2$, or an organic substituent containing from 1 to 10 carbon atoms and from 0 to 5 heteroatoms, wherein the total number of carbon and heteroatoms in all $R^1$ substituents is no more than 15.

17 Claims, 8 Drawing Sheets

CONTROL OF FUNGAL DISEASES IN THE PRODUCTION OF MUSHROOMS

BACKGROUND OF THE INVENTION

1. Field of the Invention

The present invention is related to the chemical control of Verticillium and other fungal diseases, particularly Verticillium in commercial mushroom production.

2. Description of the Background

A persistent problem in agriculture is the control of a closely related pest plant in a commercial crop. For example, although numerous herbicides exist for the control of broadleaf plants in corn, control of grass in corn is more difficult because of the closer relationship between the species.

In the mushroom industry, a similar situation exists with Verticillium. Verticillium, also known as dry bubble disease or vert, is considered to be the most significant fungal-induced disease in the mushroom industry in the United States.

A number of fungicides are available for use in commercial mushroom production in order to control Verticillium. These include Bravo, a trademarked product of SDS Biotech Corporation, Painesville, Ohio, which contains the active ingredient chlorothalonil; Mertec 340-F, a trademarked product of Merck & Company, Rahway, N.J., which contains 4'-thiazolylbenzimidazole; Benlate, a trademarked product of E.I. duPont deNemours, Wilmington, Del., which contains Benomyl, which has the systematic name of methyl 1-(butylcarboamoyl)-2-benzimidazole carbamate; and Zineb 15, a trademarked product of Wilbur-Ellis Company, Fresno, Calif., which contains zinc ethylene bisdithiocarbamate. However, this last fungicide is not available in all states because of environmental protection laws. Bravo is also not approved in all states. For example, it has only a Section 18 (emergency) registration in California, with full registration pending. In a similar manner, Sporogon 50WP, a trade-marked product of Darmycel, a division of Darlington Mushroom Lab, Rustington, West Sussex, United Kingdom, contains a prochloraz magnesium complex that is not approved for use in the United States.

Although these fungicides have been successfully used in commercial operations, continued concern over potential toxicity as well as cost makes the discovery of less toxic and more cost effective methods of treatment of Verticillium a desirable goal for the mushroom industry.

SUMMARY OF THE INVENTION

Accordingly, the present invention provides a method of controlling toxic fungal diseases in mushrooms, particularly Verticillium, comprising adding an effective fungal-disease-inhibiting amount of a compound of a formula

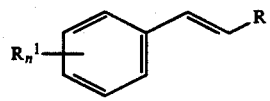

to a substrate in which mushrooms are growing or are to be grown, wherein R represents $-CH_2OH$ or $-CHO$; n is an integer from 0 to 3; and each $R^1$ independently represents OH or an organic substituent containing from 1 to 10 carbon atoms and from 0 to 5 heteroatoms, wherein the total number of carbon and heteroatoms in all $R^1$ substituents of said compound is no more than 15. These compounds are cinnamaldehyde, cinnamyl alcohol, and closely related compounds. Methods of the invention provide control of Verticillium and other fungal diseases using compounds such as cinnamaldehyde, which is known to be ingestible and is present in natural food sources, or natural products containing cinnamaldehyde or a related product, such as cinnamon bark.

BRIEF DESCRIPTION OF THE DRAWINGS

The present invention will be better understood by reference to the following detailed description of specific embodiments when considered in combination with the drawings that form part of this specification, wherein.

DESCRIPTION OF SPECIFIC EMBODIMENTS

Figure 1:
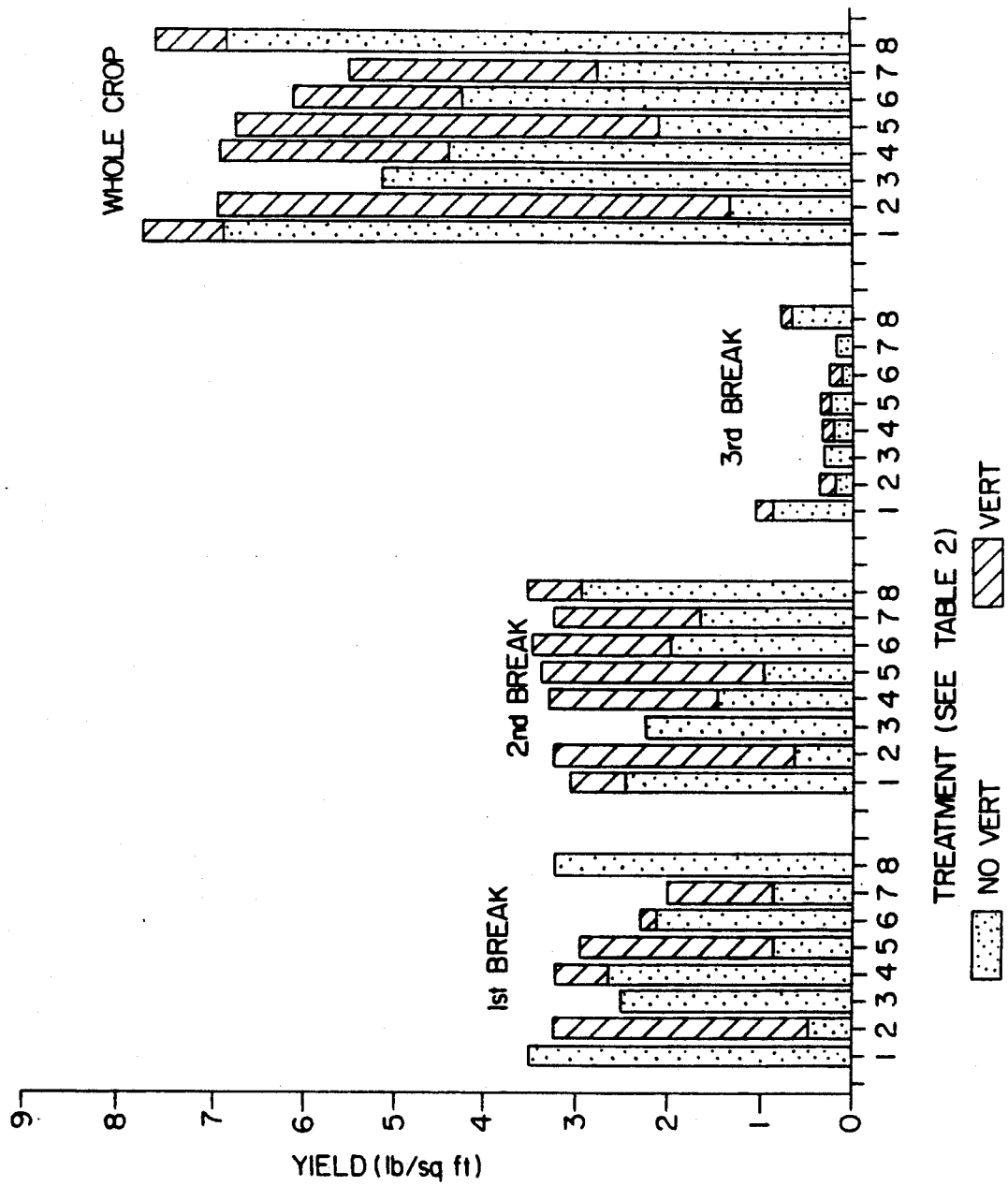
FIG. 1 is a graph showing mushroom yield for a variety of Verticillium-control treatments.

It has been discovered that cinnamaldehyde and related compounds are effective for controlling fungal diseases, particularly Verticillium, in substrates in which mushrooms grow. Although cinnamon oil was previously known to exhibit anti-fungal properties (see, for example, Mukerjee, Z. Pflanzenkr. Pflanzenschutz (1976) 83:305-308, and Bullerman, et al., J. Food Sci. (1977), 42:1107-1109), there does not appear to have been any indication of the selective toxicity that allows use of cinnamon oil and related products in the control of fungal diseases in mushrooms, which themselves are fungi.

Compounds that can be used in the practice of the present invention are those closely resembling cinnamaldehyde in structure and properties. While it has been experimentally demonstrated that cinnamic acid is ineffective in preventing growth of Verticillium, the invention is not limited to use of cinnamaldehyde alone. Other compounds that are readily converted to cinnamaldehyde (or a closely related compound with a substituent in the phenyl ring) by a biological process, such as oxidation, should be equally effective. For example, cinnamyl alcohol can readily be oxidized to cinnamaldehyde in a number of biological situations. Additionally, relatively small organic substituents can be present in the phenyl ring. Typical substituents include halogen, hydroxy, amino, and organic substituents containing from 1 to 10 carbon atoms and from 0 to 5 heteroatoms, typically the total number of carbon and heteroatoms in all substituents being no more than 15.

Preferred compounds of the invention are those having the formula

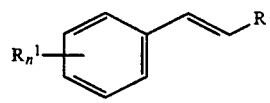

in which R represents —CH$_2$OH or —CHO; n is an integer from 0 to 3; and each R$^1$ independently represents halogen hydroxy, amino, or an organic substituent containing from 1 to 10 carbon atoms, and from 0 to 5 heteroatoms. Smaller substituents containing from 1 to 4 aliphatic carbon atoms and 0 to 1 phenyl rings are preferred. Heteroatoms are typically oxygen, nitrogen, or sulfur, and are present as ether, carbonyl, hydroxy, amine, amide, and related groups, such as those in which sulfur replaces oxygen in one of the groups named above. Particularly preferred substituents on the phenyl ring are selected from the group consisting of OH, R$^2$, OR$^2$, C(=O)R$^2$, C(=O)OR$^2$, and OC(=O)R$^2$, in which R$^2$ represents a C$_1$–C$_6$ alkyl, alkenyl, or alkynyl, optionally comprising a hydrocarbon ring when R$^2$ contains 3 or more carbons. Particularly preferred R$^2$ groups include methyl, ethyl, propyl, isopropyl, and phenyl. An especially preferred group of substituents on the phenyl ring includes hydroxy, R$^2$, and OR$^2$, in which R$^2$ is methyl or ethyl, particularly methyl. Although up to 3 substituents can be present on the phenyl ring (in addition to the substituted vinyl group characteristic of cinnamaldehyde or cinnamyl alcohol), 2 or fewer, preferably 1 or fewer, and most preferably 0, are typically present. Cinnamaldehyde is particularly preferred as it is the most effective compound tested to date.

In addition to the specific compounds of the formula set forth above, derivatives of any of these compounds that produce a compound of the formula given above upon action of a biological system on the derivative are considered to be equivalent to compounds of the invention when used in the claimed method. For example, if an ester of cinnamyl alcohol is applied to a mushroom substrate, biochemical processes will result in cinnamyl alcohol being released from the ester. Biochemical oxidations will then likely produce cinnamaldehyde. In a similar manner, acetals of cinnamaldehyde readily produce cinnamaldehyde on hydrolysis. Thus, application of a compound such as cinnamaldehyde dimethyl acetal or cinnamyl acetate to a mushroom-growth substrate would be equivalent to the practice of the present invention using cinnamaldehyde.

The method of the present invention is carried out by adding an effective fungal-disease-inhibiting amount of a compound of the invention to a substrate in which mushrooms are growing or are to be grown. The method is particularly directed to controlling dry bubble disease in commercial mushrooms. Dry bubble disease is caused by Verticillium species, particularly *V. fungicola*. However, the method of the invention is also useful in treating Trichoderma, especially infections of *T. viride*, and *T. kaningii*. Additional fungal diseases of mushrooms that can be treated by the method of the present invention include those caused by *Mycogone perniciosa, Hypomyces roseilus, Diehliomyces microsporus,* and *Mortierella bainieri.*

The amount of a fungicidal compound that should be applied to a substrate will vary with the degree of infestation (and to some extent with the formulation and/or specific compound being used) and therefore must be empirically determined for best results. However, an initial concentration of from 1 to 200 ppm, preferably from 1 to 100 ppm, and more preferably from 5 to 50 ppm of the substrate (when the fungicidal compound is uniformly mixed with the substrate), is suitable for an initial treatment. The dose can then be raised or lowered depending on the fungal disease being treated and the effect on production of mushrooms (if any).

Although uniform mixing with the casing layer may be more effective in controlling Verticillium infections within the interior of the compost, effective fungal disease control can also be achieved by applying a fungicidal compound of the invention to a surface of the mushroom substrate (typically an upper surface of the casing layer in a container in which commercial mushrooms are being grown). As discussed above, empirical modification of the dose rate may be required. However, an initial dose rate of from 0.028 to 5.6 g/m$^2$, preferably from 0.028 to 2.8 g/m$^2$, and more preferably 0.28 to 1.4 g/m$^2$ will provide an effective initial application, which can be adjusted if appropriate. These calculations can be converted as appropriate to account for the carrier or other inactive ingredients; e.g., 2.8 g/m$^2$ of cinnamaldehyde would be equal to about 160 g/m$^2$ of cinnamon bark, or about 15 g/ft$^2$.

The method of the invention can be used with any composting method or other technique used in the production of mushrooms. A general review of mushroom cultivation is set forth in Flegg, et al., Eds., *The Biology and Technology of the Cultivated Mushroom*, John Wiley & Sons, New York, 1985. Also see commonly assigned U.S. application Ser. No. 114,226, filed Oct. 26, 1987, which discusses various processes used in the production of mushrooms, as well as new composting processes.

Compounds described herein can be added at any point in the preparation of a mushroom-growth substrate (casing layer). For example, active compounds can be added during the initial casing application stage so that they are present throughout the casing layer. Since casing can involve numerous mechanical mixing operations, compounds of the invention will be well dispersed through the substrate when used in this manner. However, compounds can also be added to the casing layer after it is added to beds or containers in which mushrooms will be grown, including in the presence of mature mushrooms. Compounds can be added either as pure components or as pure compounds in the presence of a carrier for ease of handling.

Compounds of the invention can be applied as solids, liquids, or vapors. Many of the compounds have high vapor pressures and are relatively volatile. Solutions and emulsions used in the form of sprays represent a preferred form in which compounds of the invention can readily be applied to large areas of casing layer surface with minimal effort. An example of a suitable emulsion is a composition comprising cinnamaldehyde in an aqueous solution containing 1% Tween 80 and ethylenediamminetetraacetic acid (EDTA). This composition produces an average droplet size of 50 microns and remains as an emulsion for about 30–60 minutes. Stabilizing agents, such as xanthan gum, can be used to improve the longevity of the emulsion.

Likewise, preparation of a compound as a solid composition (e.g., mixed with other casing components) for application during the casing process is also a useful technique. Compounds can also be formulated as dusts on solid carriers, such as calcium silicate. The use of active aldehydes on such solid materials can lead to oxidation. However, the experiments described in more detail in the examples that follow indicate that not all of the active material is oxidized to the corresponding inactive acid when formulated in this manner. Antioxidents, such as butylatedhydroxyanisole (BHA), butylatedhydroxytoluene (BHT), $\beta$-mercapto-ethanol, and hydroxyquinoline, can be used to reduce undesirable oxidation.

Although application of compounds of the invention is preferred during either the casing process or a stage of the mushroom growing process after casing, the compounds may also be applied in any stage of the mushroom growing process before casing.

When the fungicidal compound of the invention is a component of a natural product, as are cinnamaldehyde, cinnamyl alcohol, and a number of related compounds, the natural product can be used without modification. For example, cinnamaldehyde can be added to a substrate as a composition containing cinnamon oil or cinnamon bark. Cinnamon oil is about 80–90% cinnamaldehyde, and cinnamon bark contains about 0.8 to 4.5% cinnamaldehyde. Dosage amounts are adjusted based on the content of active component (or components) present in the natural product. Cinnamyl alcohol and related compounds are also present in cinnamon oil and cinnamon bark.

When there is a desire to add active compounds in the most defined manner possible, they are best added in the substantial absence of other components that were present in the original natural product, such as cinnamon oil, from which the active component may have been obtained. Substantial absence preferably means that no more than 10%, preferably no more than 1%, of components that are present in the natural product other than the specific active compound being added are present in the composition being used.

The method of the present invention can be used with a wide variety of mushrooms including *Agaricus brunnescens* Peck c *A. bisporus* (Lange) Imbach (cultivated mushroom), *A. campestris, A. bitorquis, A. augustus, Armillaria mellea, Pleurotus ostreatus, Volvariella volvacea, Coprinus comatus, Morchella esculenta, M. angusticeps, M. conica, M. crassipes, Lentinus edodes,* and other edible fungi. *Agaricus* species, particularly *A. brunnescens,* are preferred mushrooms on which the method is practiced.

The invention now being generally described, a more complete understanding can be obtained by reference to the following specific examples, which are included for purposes of illustration only and are not intended to be limiting unless otherwise specified.

EXAMPLE 1

Effect of Cinnamon Oil on Verticillium Growth

In a first experiment, Verticillium spores isolated from a commerical mushroom compost were inoculated onto Petri dishes containing cellophane agar medium. This and other media used in these Examples are described in detail in the section titled "Description of General Techniques." The media also contained cinnamon oil at 1,000, 500, 100, 50 and 10 parts per million. All concentrations of 50 ppm and higher were totally effective in inhibiting Verticillium growth. A concentration of 10 ppm produced approximately 50% inhibition.

EXAMPLE 2

Effect of Cinnamon Oil on Mushroom Growth (*A. bisporus*)

The effect of cinnamon oil on the growth *A. bisporus* on Rapers Complete Media was determined. At a concentration of 20 ppm cinnamon oil, no inhibition of *A. bisporus* was observed. At this concentration there was 80% inhibition of Verticillium growth. At higher concentrations of cinnamon oil (30, 50 and 100 ppm) inhibition of *A. bisporus* did occur (54, 37, and 100% inhibition, respectively, in this experiment).

EXAMPLE 3

Effect of Cinnamon Oil on Trichoderma Growth

The effect of cinnamon oil on a Trichoderma species obtained from a commercial mushroom compost was tested. The same procedure was used as in Example 1. Concentrations of 20, 30, 50 and 100 ppm cinnamon oil were used. Percent inhibition for these concentrations were 18, 92, 100, and 100%, respectively.

EXAMPLE 4

Effect of Encapsulated Cinnamon Oil on Verticillium Growth

In an experiment designed to determine whether the composition or form of the active ingredient had any effect on control of Verticillium, cinnamon oil encapsulated in malto-dextrin was used in an inhibition assay. Beginning with this experiment, mushroom agar was used in place of Cellophane Agar Medium. The encapsulated cinnamon oil, known as Borden Caps, is a commercial food product sold by the Borden Company as an encapsulated flavor. Upon hydration, the encapsulating material dissolves, releasing the cinnamon oil. A second encapsulated cinnamon product, F/C Cinnamon from McCormick-Stange containing 20% cinnamon oil, was also tested. Encapsulated cinnamon oil in varying concentrations was added to mushroom agar and compared to agar containing no cinnamon oil. For Borden Caps, 200, 300, 500, and 1,000 ppm Caps were used in the agar. For McCormick-Stange encapsulated cinnamon, 100, 150, 250, and 500 ppm were used. Verticillium spores were added to the growth media. The degree of growth of the spores was rated after one week.

Borden Caps were completely effective in inhibiting Verticillium at 300 ppm. This corresponds to an active ingredient level of 30 ppm cinnamon oil. McCormick-Stange encapsulated cinnamon oil was effective at 250 to 500 ppm. This corresponds to an active ingredient level of 50 to 100 ppm cinnamon oil. As these results were within the range of experimental error of this example, there appears to be little effect on the result by the type of composition as long as the cinnamon oil (or other active ingredient) is readily released into the mushroom growth medium.

EXAMPLE 5

Contact vs. Vapor Effects of Cinnamon Oil on Verticillium Growth

This experiment was done using a two-compartment Petri dish (split plate). One-half of each plate was poured with mushroom media, and the other half was poured with mushroom media mixed with 50, 100, 500, and 1,000 ppm cinnamon oil. Verticillium spores were added to the half of the split plate which was not treated with cinnamon oil. After several days incubation, the degree of growth was determined. Very little inhibition was seen at 50 or 100 ppm cinnamon oil. Approximately 84% inhibition was seen for 500 ppm cinnamon oil with complete inhibition at 1,000 ppm cinnamon oil. As these numbers are considerably higher than previous examples which showed direct contact, direct contact appears to be more effective in controlling Verticillium growth, although contact with vapors remains effective when sufficient volatile reagent is provided.

EXAMPLE 6

Comparison of Cinnamon Oil to Cinnamaldehyde

Cinnamaldehyde was used instead of cinnamon oil at 10, 20, 30, 50, 100 and 500 ppm cinnamaldehyde in a number of experiments. Verticillium spores were added to the media, and the degree of growth was recorded after several days of incubation. Complete inhibition was seen at 50 ppm and higher, with 10 ppm providing approximately 48% inhibition. These results closely parallel the results seen for cinnamon oil in Example 1 taking into consideration that cinnamon oil typically contains about 80-90% cinnamaldehyde. It therefore appears that cinnamaldehyde is acting as the principal active ingredient in cinnamon oil which inhibits Verticillium growth.

EXAMPLE 7

Activity of Compounds Related in Structure to Cinnamaldehyde

A number of compounds with structures similar to cinnamaldehyde were tested for inhibition of Verticillium growth using the same technique described in Example 4. Compounds were 4-hydroxy coumarin, umbelliferone, p-coumaric acid, m-coumaric acid, o-coumaric acid, 4-hydroxy-3-methoxycinnamic acid, and 3-hydroxy-4-methoxycinnamic acid. These compounds are either carboxylic acids or are cyclic esters of carboxylic acids. None of the compounds tested showed significant inhibition of Verticillium growth at 20, 50, or 100 ppm.

EXAMPLE 8

Effect of Cinnamon Oil on A. Bisporus Growing in Compost/Casing Layer

The objective of this experiment was to determine whether cinnamon oil reduced mushroom yield too much for it to be used as a treatment for Verticillium and other fungal diseases. Since Verticillium typically reduces quality and yield, a slight loss in yield while controlling Verticillium is acceptable.

Individual commercial mushroom trays were treated in the manner set forth in Table 1.

TABLE 1

Determination of Possible Cinnamon Oil Phytotoxicity to *A. bisporous* Growing in Trays

| T# | Treatment | Treat Added | Vert Added | Yield (% of control) |
|---|---|---|---|---|
| T1 | Control | — | — | 100 |
| T2 | Control + Verticillium | — | C22 | 99 |
| T3 | Cinnamon Oil | C22 | — | 92 |
| T4 | Cinnamon Oil + Verticillium | C22 | C22 | 88 |
| T5 | Cinnamon Oil | C16,C22,C32 | — | 91 |
| T6 | Cinnamon Oil + Verticillium | C16,C22,C32 | C22 | 86 |

TABLE 1-continued

Determination of Possible Cinnamon Oil Phytotoxicity to *A. bisporous* Growing in Trays

| T# | Treatment | Treat Added | Vert Added | Yield (% of control) |
|---|---|---|---|---|
| T7 | Sporogon | C22 | — | 93 |
| T8 | Sporogon + Verticillium | C22 | C22 | 96 |

All cinnamon oil concentrations were 100 ppm. Sporogon was added at 2 oz/1000 sq. ft. Application times were noted as the number of days after casing with casing day counted as zero (C0). Treatments added on 22 days after casing (C22) were added 4 hrs prior to Verticillium. Verticillium inoculated in this experiment (and later experiments) was isolated from commercial mushrooms on 1/87. The concentration of Verticillium added was $6 \times 10^6$ spores/ft$^2$.

All cinnamon oil concentrations were 100 ppm. Cinnamon oil was mixed thoroughly with water using a blender. The mixture was sprayed onto the trays using a spray tip attached to a syringe. The quantity "ppm" refers to the number of parts per million by weight based on the wet weight of casing soil in the trays. The cinnamon oil mixture was sprayed only on top of the casing layer. The commercial fungicide Sporogon was diluted and sprayed on the surface of the casing layer at a rate equivalent to two ounces of undiluted Sporogon per 1,000 sq. feet. Application times are indicated in Table 1 as a number of days after casing, with casing day counted as zero (C0). Treatments added 22 days after casing (C22) were added 4 hours prior to addition of Verticillium. The Verticillium used in this and later described experiments was isolated from a commercial mushroom production facility. Verticillium was diluted in water so that a specific amount of water plus spores could be added to each tray. This water suspension was sprayed onto trays in the same manner as cinnamon oil described above to provide a Verticillium concentration of $6 \times 10^6$ spores/ft$^2$.

Three breaks were harvested, and the effect of cinnamon oil was evaluated based on the result of the whole crop over three breaks. Although yields with cinnamon oil were lower than control yields (Table 1), the reduction in yield was acceptable in view of the control of Verticillium. Verticillium control was not quantitated in this experiment. See Examples 9 and 10 for quantitation of Verticillium control.

EXAMPLE 9

Evaluation of Verticillium Control

Commercial mushrooms were grown in trays in the same manner as in Example 8. Cinnamon bark was applied at various times and rates as shown in Table 2, which also shows controls used in the experiment.

TABLE 2

Application Schedule for Control of Verticillium

| T# | Treatment | Treatment Applied | Verticillium Applied |
|---|---|---|---|
| T1 | Control | — | — |
| T2 | Control + vert | — | — |
| T3 | Sporogon | C17,C25,C30 | C18 |
| T4 | Cinn bark (500 ppm) | C19,C27,C32 | C18 |
| T5 | Cinn bark (500 ppm) | C17,C25,C30 | C18 |
| T6 | Cinn bark (2,500 ppm) | C19,C27,C32 | C18 |
| T7 | Cinn bark (2,500 ppm) | C17,C25,C30 | C18 |
| T8 | Tween 80 (2 oz/100 gal) | C17,C25 | — |

Figure 2:
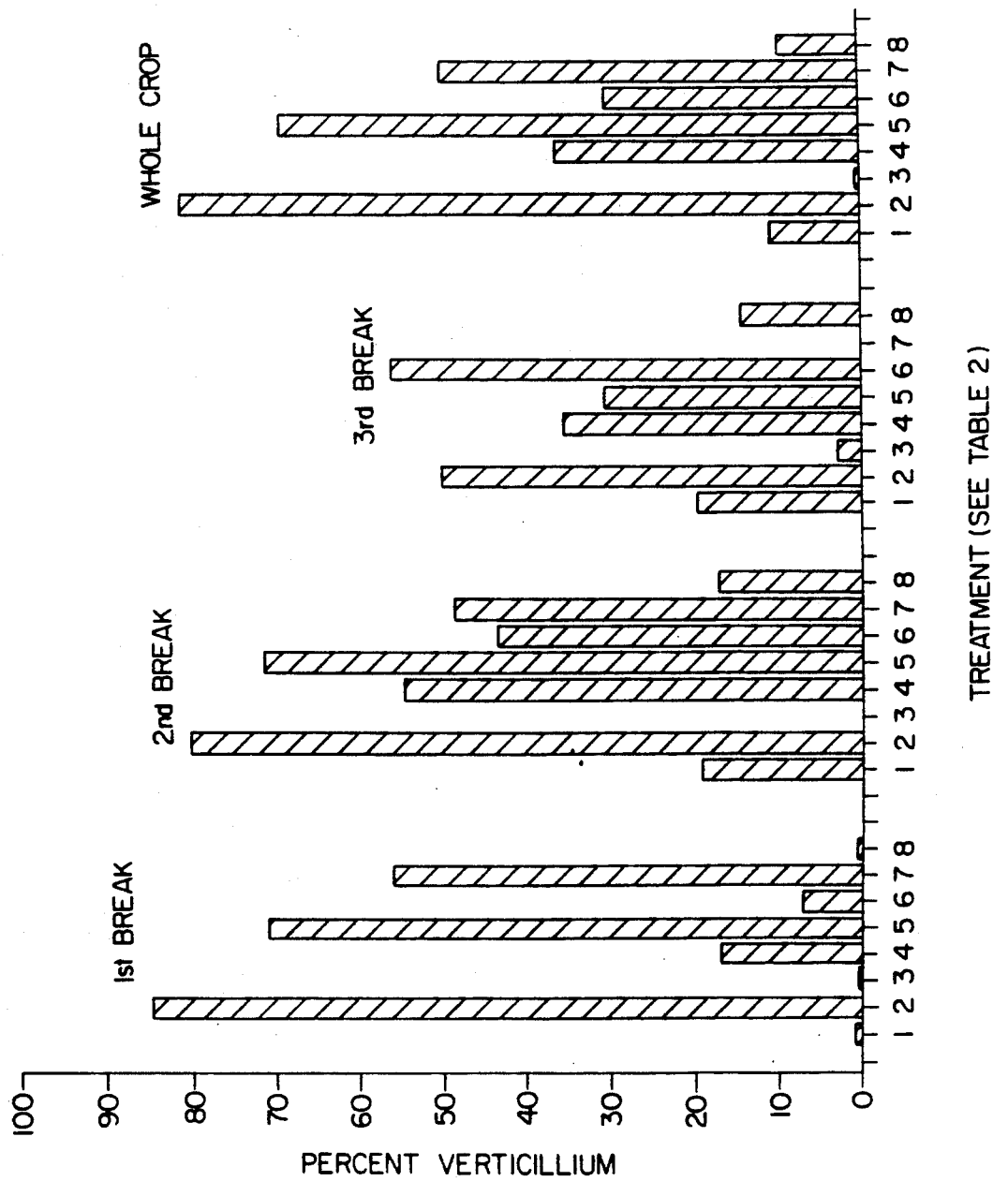
FIG. 2 is a graph showing percent mushrooms infected by Verticillium for a variety of Verticillium-control treatments.

The cinnamon bark used contained approximately 2% cinnamon oil. The two cinnamon bark concentrations (2,500 ppm and 500 ppm) correspond to 50 ppm and 10 ppm cinnamon oil. Two application points were used for comparison. Sporogon was added at 4 oz/1,000 ft$^2$ at C17 (17 days after casing) and 2 oz/1,000 ft$^2$ at C25 and C30. The concentration of Verticillium spores was 2.7×10$^5$ spores/ft$^2$. Yield comparisons are shown in FIG. 1. A plot of percent diseased mushrooms is shown in FIG. 2.

It can be seen that Sporogon (treatment 3) was applied much closer to first break in this experiment. Accordingly, the Sporogon treatment resulted in numerous deformed mushrooms in the first break (data not shown). While this application schedule produced very little disease, the production of deformed mushrooms is disadvantageous.

Although the reduction in disease outbreak was not as great for cinnamon bark as for Sporogon, significant reduction in disease was seen, especially for cinnamon bark added late in incubation (after Verticillium inoculation).

Test 8, Tween 80 applied alone, was included as an evaluation of the possibility of using Tween 80 as a carrier for cinnamon oil (such a composition is shown in Example 10).

EXAMPLE 10

Variation in Timing of Application of Cinnamon Oil

Mushrooms were grown in the same manner as in Example 8. Variations in treatment are shown in Table 3.

TABLE 3
Determination of Optimal Timing of Application of Cinnamon Oil

| T# | Treatment | Treatment Applied | Verticillium Applied |
|---|---|---|---|
| T1 | Control | — | — |
| T2 | Control + vert | — | C14 |
| T3 | Sporogon | C9,C23 | C14 |
| T4 | Cinn bark (2,500 ppm) | C9,C23 | C14 |
| T5 | Cinn bark (2,500 ppm) | C15,C23 | C14 |
| T6 | Cinn oil + Tween 80 | C15,C23 | C14 |
| T7 | Control + vert | — | C22 |
| T8 | Cinn bark (2,500 ppm) | C23 | C22 |

For T3, Sporogon was applied at 4 oz/1,000 ft$^2$ on C9 and 2 oz/1,000 ft$^2$ on C23. For T6, cinnamon oil was added in an aqueous composition containing 50 ppm cinnamon oil and 2 oz/100 gal Tween 80. Cinnamon bark corresponds to approximately 50 ppm cinnamon oil at the application rate shown. Verticillium was inoculated at approximately ten times the rate shown in Example 9; 2.7×10$^6$ spores/ft$^2$ on C14 and 8.6–10$^5$ spores/ft$^2$ on C22.

Figure 3:
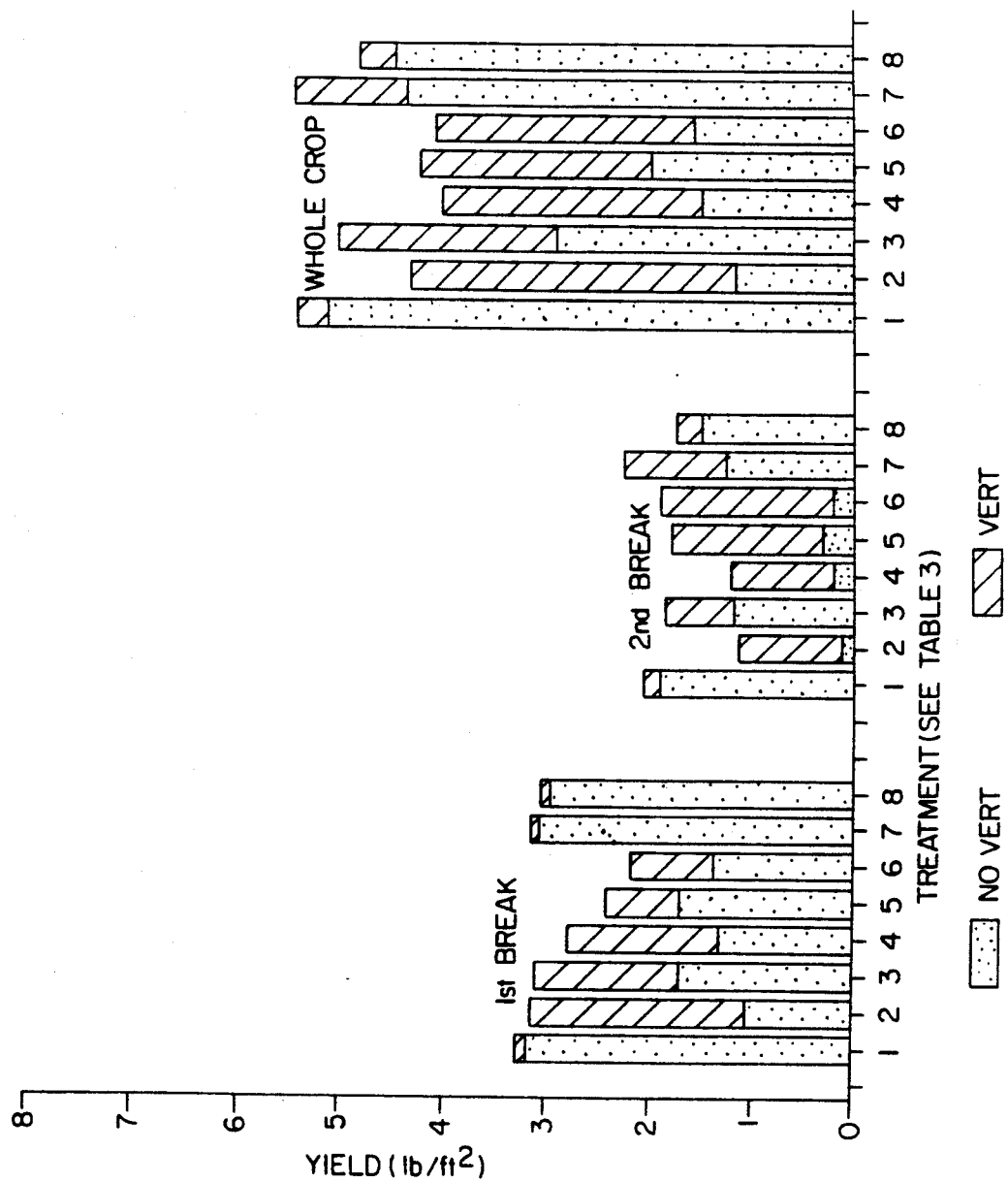
FIG. 3 is a graph showing mushroom yield for a variety of Verticillium-control treatments.
Figure 4:
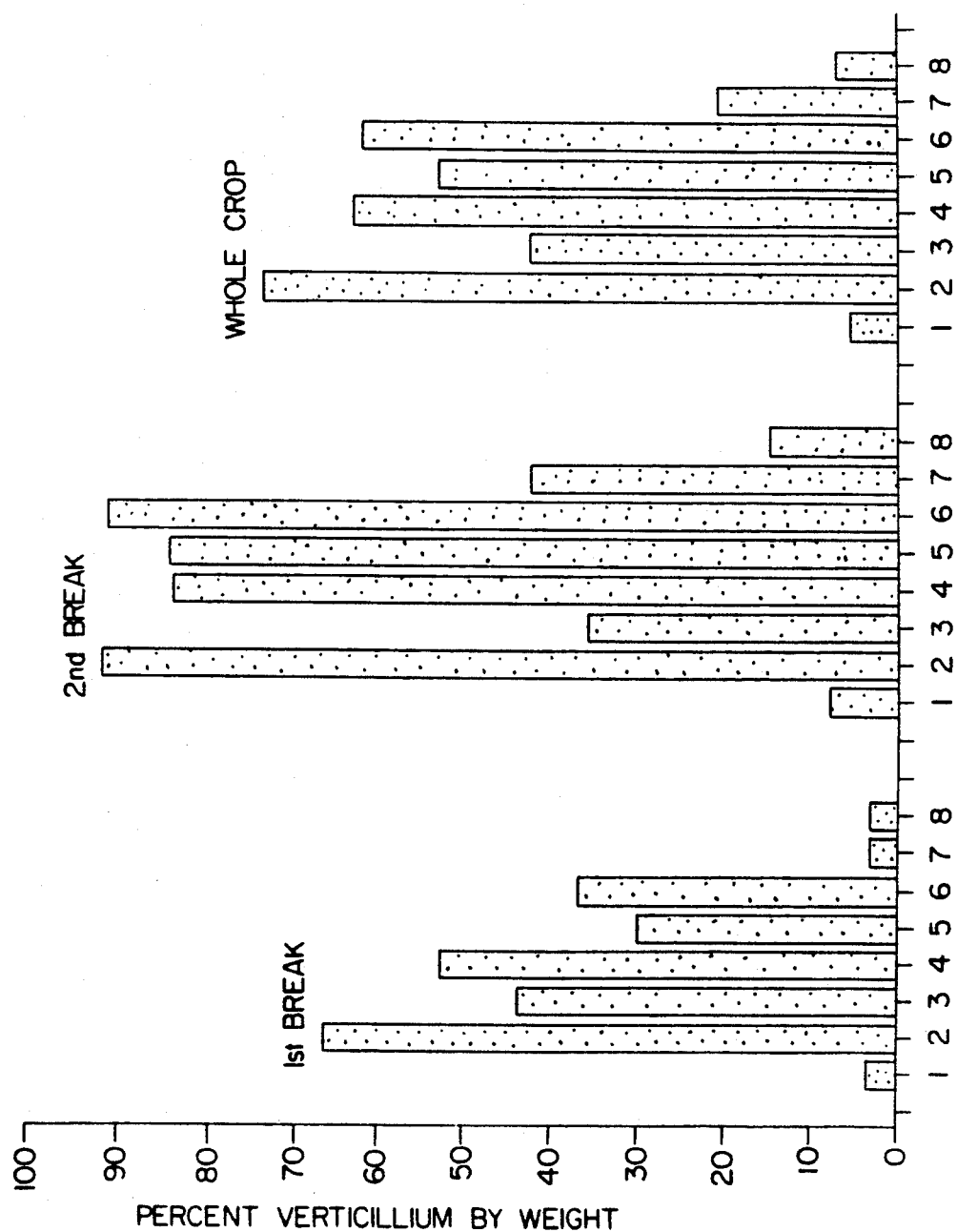
FIG. 4 is a graph showing percent mushrooms infected by Verticillium for a variety of Verticillium-control treatments.

Yield comparisons are shown in FIG. 3 with percent diseased mushrooms shown in FIG. 4.

In this experiment, the Verticillium inoculum level was ten times larger than in Example 9. Disease control in the second break was not as good as that in the previous example. In the first break, cinnamon bark added just prior to first break (treatment 5) gave the lowest percent disease. All the cinnamon bark treatments (treatments 4, 5, and 6) had lower yields than control but also showed less percent disease than the control plus Verticillium (treatment 2). Treatments 7 and 8 involved addition of Verticillium and cinnamon bark after first break. For the second break, treatment 3 (Sporogon) and treatments 4, 5 and 6 (cinnamon bark and cinnamon oil) showed poorer disease control than for Example 9, apparently because of the higher level of Verticillium inoculum.

EXAMPLE 11

Further Variation in Timing of Application and Concentration of Cinnamon Oil

Mushrooms were grown in the same manner as in Example 8. Variations in treatments are shown in Table 4.

TABLE 4
Further Determination of Optimal Timing of Application of Cinnamon Oil

| T# | Treatment | Treatment Applied and Rate | Verticillium Applied |
|---|---|---|---|
| T1 | Control | — | — |
| T2 | Control + vert | — | C15 |
| T3 | Bravo | Labeled Rate and Modified Timing | C15 |
| T4 | Cinn Bark | 1250 ppm at Casing<br>1250 ppm at Flush<br>2500 ppm between each Break | C15 |
| T5 | Cinn Bark | 2500 ppm at Casing<br>2500 ppm at Flush<br>2500 ppm between each Break | C15 |
| T6 | Cinn Bark | 1250 ppm at Casing<br>1250 ppm between each Break | C15 |
| T7 | Cinn Bark | 500 ppm every 3rd day up to pin<br>500 ppm between each Break | C15 |
| T8 | Cinn Bark | 2500 ppm after First Break<br>3750 ppm after Second Break | C15 |

For T2, Bravo was applied at the labeled rate on C20, C26, and C34. Cinnamon bark at 3750 ppm, 2500 ppm, 1250 ppm, and 500 ppm is equivalent to a cinnamon oil concentration of 75 ppm, 50 ppm, 25 ppm and 10 ppm, respectively. Verticillium was inoculated at 5.4×10$^4$ spores/ft$^2$ on C15.

Figure 5:
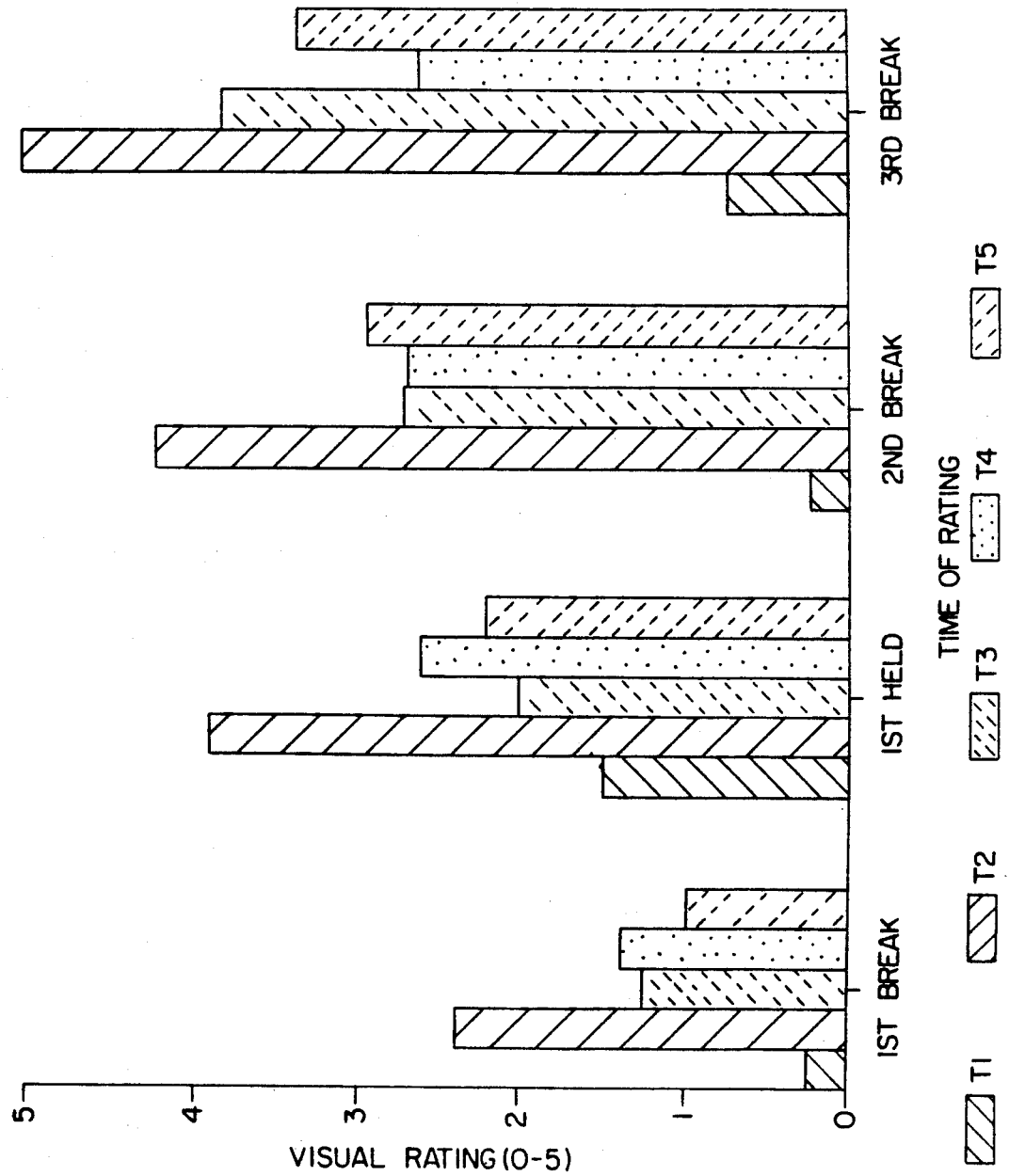
FIG. 5 is a graph showing visual disease ratings for a variety of Verticillium-control treatments.
Figure 6:
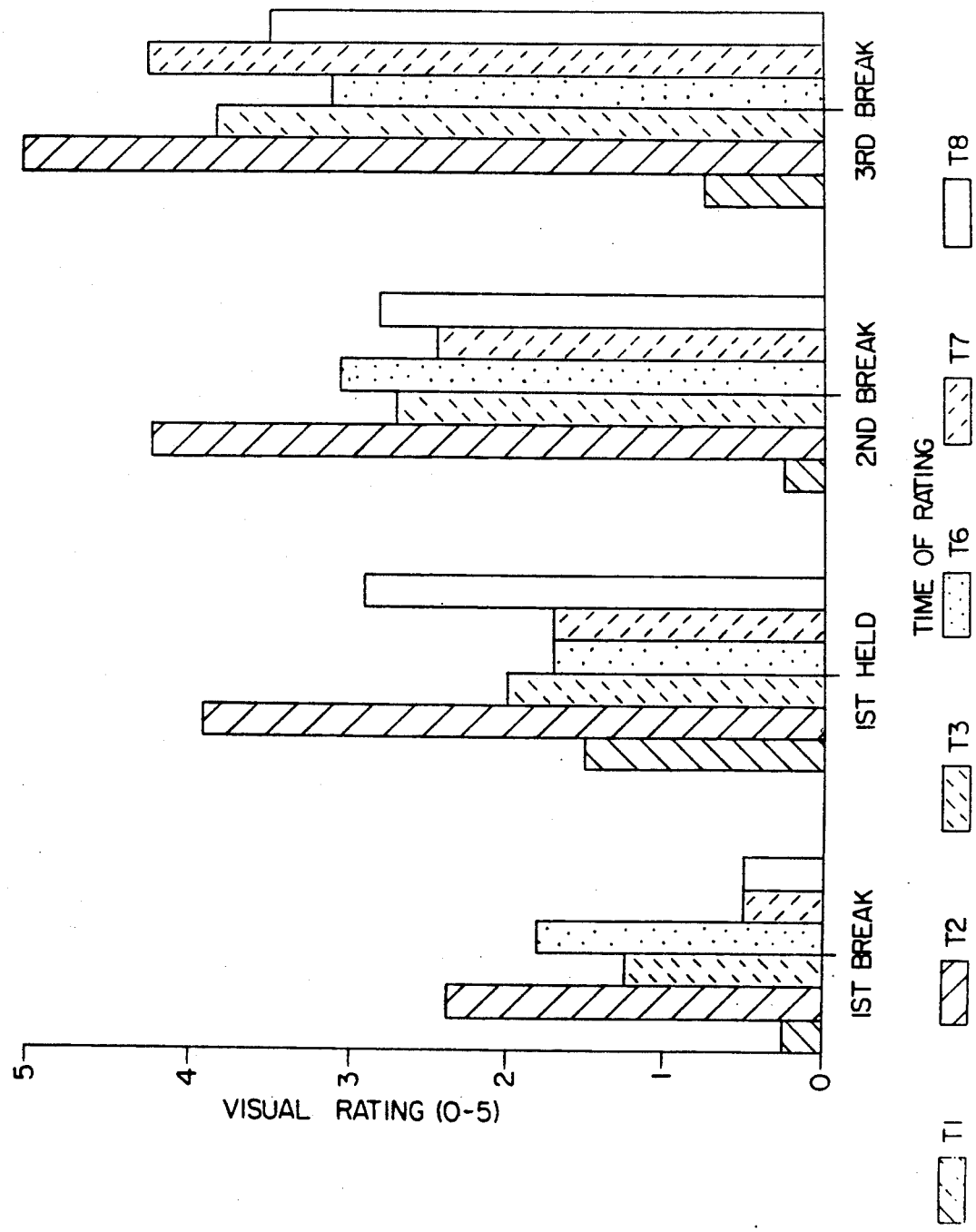
FIG. 6 is a graph showing visual disease ratings for a variety of Verticillium-control treatments.
Figure 7:
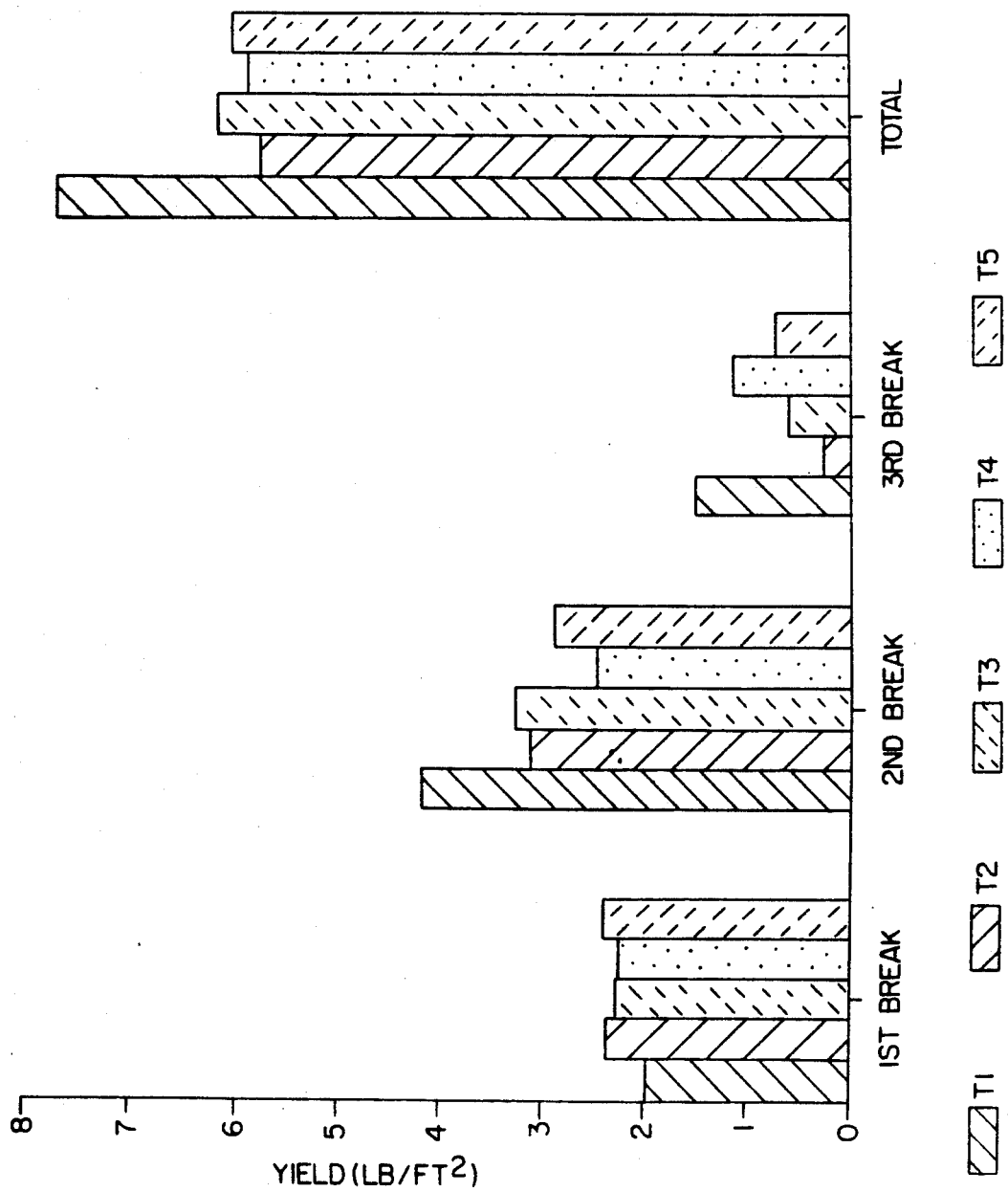
FIG. 7 is a graph showing mushroom yield for a variety of Verticillium-control treatments.
Figure 8:
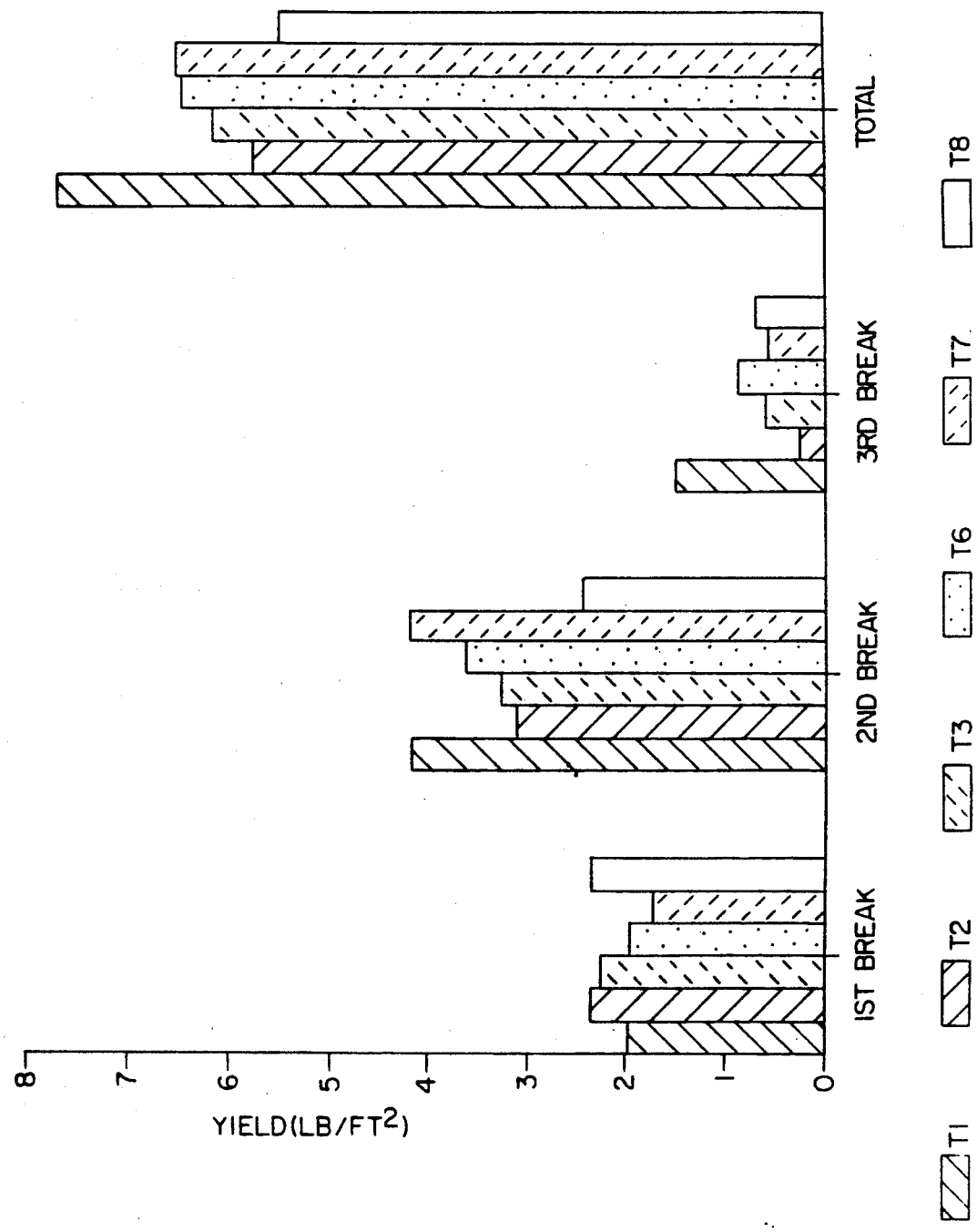
FIG. 8 is a graph showing mushroom yield for a variety of Verticillium-control treatments.

Yield comparisons are shown in FIG. 7 and 8 with a visual disease ratings shown in FIG. 5 and 6. The disease ratings used in FIG. 5 and 6 are as follows: 0=none, 1=slight, 2=mild, 3=medium, 4=heavy, 5=severe.

As the result of the high level of disease in Example 10, this experiment was inoculated at a rate lower than Example 9. The best disease control on first break was with cinnamon bark treatment T7. T8 did not have treatment before first break. Vert was difficult to rate on first break, so it was held two days and rated again to verify results. Other treatments were comparable to Bravo except for T6. First break was harvested and then held at 25° C. and 50% relative humidity for 2 days before evaluating once again. Under those conditions of post-harvest storage, two of the five cinnamon treatments (T6 and T7) controlled dry bubble better than the Bravo control. On second break, all control measures performed in a comparable manner; however, on third break where the disease pressure was at its peak, all the cinnamon bark treatments, expect T7, performed better than Bravo. The highest total yield with Verticillium added were cinnamon bark treatments T6 and T7.

EXAMPLE 12

Cinnamaldehyde Formulated as a Dust

Cinnamaldehyde as a "dry liquid" or dust at a rate of 50% active ingredient has been highly successful in full room trials at a commercial mushroom production facility. The formulation was prepared by spraying 50 pounds of active cinnamaldehyde onto 50 pounds of a synthetic calcium silicate, such as Manville "Micro-cel" in a ribbon blender. Some (but not all) of the cinnamaldehyde oxidized to the inactive acid. This "dry liquid" formulation was tested both as a dust at a rate of 5 pounds per 7400 ft$^2$ surface bed area and as a bed drench, whereby 5 pounds of the formulated material was added to 200 gallons of water in a continuously aggitated tank, the water suspension then being applied during irrigation.

These formulations were used in a commercial mushroom production facility known to be contaminated with Verticillium. Significant reduction (not quantitated) in Verticillium infection was noted. Additionally, there was less spotting of the mushrooms themselves when cinnamaldehyde was used in the dry formulation than had been seen previously when cinnamaldehyde was sprayed directly onto mushroom beds.

DESCRIPTION OF GENERAL TECHNIQUES USED IN PRECEDING EXAMPLES

In vitro Media Formulas

Cellophane Agar

This medium is a variation of that described by Taylor, *Can. J. Botany* (1969) 47:737–740.

| Recipe Summary for 1 Liter | |
|---|---|
| Cellophane (untreated) | 20 g (PT-clear cellophane, Zellerbach) |
| Polygalacturonic acid | 2 g |
| 2M MgSO$_4$ 7H$_2$O | 0.5 ml |
| 2M KNO$_3$ | 5.0 ml |
| 1M KHPO$_4$, pH 7.0 | 10.0 ml |
| Tergitol-NPX | 1.0 ml |
| Agar | 15 g |
| Chloramphenicol | 250 mg (dissolve in ethanol) |
| Penicillin-G | 200 mg |
| Streptomycin sulfate | 200 mg |
| H$_2$O | to 1,000 ml |

Preparation

1. Cut the cellophane into sufficient pieces so that it can be stuffed in a 1½ liter Erlenmeyer flask or in a large beaker and add about 750 ml distilled water. Autoclave for 20 min. Decant the extract into a graduated cylinder and add several rinses of water to the cellophane; shake well and decant the rinse water into the extract until a total of 1.0 liter of exract plus rinse water have been collected.

2. To the 1 liter of cellophane extract add with stirring the polygalacturonate*, the MgSO$_4$, KNO$_3$, KHPO$_4$, the biotin and the tergitol. Stir well (magnetically) until the tergitol is fully dissolved. Then add the agar and autoclave for 20 min. Also autoclave an assembled Sweenex millipore filter unit (0.22 m).

* If polygalacturonic acid is used rather than sodium polygalacturonate the solution should be adjusted with 1.0 M KOH to pH 7.0±0.1 (approximately 10 ml).

3. Place autoclaved, partially cooled, media on stir plate and add 250 mg chloramphenicol which as been dissolved in a small amount of 95% ethanol in a sterile container. With a Sweenex millipore filter add 200 mg penicillin-G and 200 mg streptomycin sulfate dissolved in a small volume of water (2 to 5 ml).

4. Stir thoroughly and pour plates.

| Rapers Complete Media | |
|---|---|
| Glucose (dextrose) | 20.0 g |
| Peptone | 2.0 g |
| Yeast extract | 2.0 g |
| MgSO$_4$ | 0.5 g |
| KH$_2$PO$_4$ (monobasic) | 0.46 g |
| K$_2$HPO$_4$ (dibasic) | 1.0 g |
| Bacto-Agar | 20.0 g |
| H$_2$O | to 1,000 ml |

Mix all dry ingredients together, add enough distilled water to make a one-liter solution. Autoclave media for 25 min. Cool slightly, then pour plates.

| Mushroom Agar | |
|---|---|
| Mushroom extract | 25.0 ml |
| KH$_2$PO$_4$ (monobasic) | 1.5 g |
| K$_2$HPO$_4$ (dibasic) | 4.0 G |
| Agar | 15.0 G |
| Polygalacturonic acid | 2.0 g |
| Chlortetracycline | 50.0 mg |
| Chloramphenicol | 50.0 mg |
| Streptomycin sulfate | 50.0 mg |
| H$_2$O | to 1,000 ml |

1. Place fresh mushrooms in a blender until blender is half full. Add enough distilled water to start blender. Blend mushrooms to a puree, then strain through 4 layers of cheesecloth. This mushroom extract may be prepared ahead and frozen in glass screw-cap tubes.

2. Mix all ingredients (except chlortetracycline, chloramphenicol, and streptomycin sulfate) in a flask. Add enough water to make a 1-liter solution. Autoclave for 25 min. Allow solution to cool slightly (until flask is warm). Mix chlortetracycline, chloramphenicol, and streptomycin sulfate with small amount of 95% ethanol, then add this to media. Mix media by swirling flask, then pour plates.

PILOT PLANT STANDARD GROWING PARAMETERS

Compost

Phase I and Phase II compost preparation and pasteurization was carried out at Monterey Mushrooms Inc., Watsonville, Calif., using standard commercial practices.

Spawning

Each crop grown in the pilot plant consisted of 32 wooden trays. The inside measurements of the trays were as follows: 18" long, 15" wide and 7½ high. Each tray had a total growing surface of 1.875 ft$^2$.

At spawning each tray was filled with 39 lbs of fresh pasteurized, commercially prepared compost as described above. The normal water content was 70%. The dry weight of compost used is 6.24 lbs/ft$^2$. To this compost, spawn (Amycel U-1) and supplement (Spawn Mate IISE) was added and thoroughly mixed. The amount of spawn used was 2.75% of the dry weight of compost. The amount of supplement used was 5% of the dry weight of compost.

Spawn Run

During spawn run, the air temperature was maintained between 68°-74° F. This was done to maintain compost bed temperatures between 78°-82° F. During spawn run relative humidity was kept at 90%. Carbon dioxide levels are kept between 10,000-15,000 ppm. Spawn run was for 13 days at which time the trays were cased.

Casing and Production

The trays were cased at a depth of 1¾" using standard commercial casing material used at the Monterey Mushrooms Inc., Watsonville, Calif. Daily applications of water were made during the first 4 days bringing the moisture level in the casing to field capacity. On day 5 or 6 the surface of the casing layer was "scratched" to redistribute the mycelial growth. This facilitates better and more even pinning by eliminating areas that may have become "sealed" during watering or may be of uneven depth. Bed temperatures and $CO_2$ levels were maintained at 78°-80° F. and 10,000-15,000 ppm, respectively, until flushing. At flush the air temperature was dropped from 70°-72° down to 60°-62°. This caused the bed temperatures to drop to 68°. After 24 hours, the air temperature was then raised to 64° which held the bed temperature in 67°-69° range until production began.

The $CO_2$ concentration was maintained at 10,000-15,000 ppm until flushing at which time the concentration was brought down to 1,200 ppm. This concentration of $CO_2$ was achieved within 10-15 hours.

After flushing the $CO_2$ level was raised slightly to 1400-1500 ppm. It was maintained in this range throughout production. During production the air temperature was maintained between 60°-66° F. in order to keep the bed temperatures between 68° and 70° F. Depending on the experiment, harvesting occured over 3-4 breaks.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of controlling toxic fungal diseases in mushrooms infected with a fungal disease, comprising: adding an effective fungal-disease-inhibiting amount of a compound of the formula

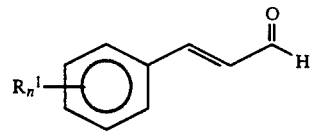

to a substrate in which mushrooms are growing or are later grown, wherein n is an integer from 0 to 3 and each $R^1$ independently represents halogen.

2. The method of claim 1, wherein n is 0 or 1.
3. The method of claim 1, wherein n is 0.
4. The method of claim 1, wherein said mushrooms belong to an Agaricus species.
5. The method of claim 1, wherein said fungal disease is Verticillium.
6. The method of claim 1, wherein said fungal disease is Trichoderma.
7. The method of claim 1, wherein said amount of said compound comprises from 1 to 200 parts per million parts of said substrate and said compound is uniformly mixed with said substrate.
8. The method of claim 1, wherein said amount comprises from 0.028 to 5.6 g/m² applied to an upper surface of said substrate.
9. The method of claim 1, wherein said compound is added to said substrate prior to spawning.
10. The method of claim 1, wherein said compound is added to said substrate after spawning.
11. The method of claim 1, wherein said compound is added in the presence of mature mushrooms.
12. The method of claim 1, wherein said compound is added in a composition containing cinnamon oil.
13. The method of claim 1, wherein said compound is added in a composition containing cinnamon bark.
14. The method of claim 1, where said compound is substantially free of natural cinnamon oil.
15. The method of claim 1, wherein said compound is added to said substrate in a formulation comprising said compound dried onto an agronomically inert solid carrier.
16. The method of claim 1, wherein said solid carrier is a calcium silicate.
17. The method of claim 1, wherein said fungal disease is caused by Mycogone perniciosa, Hypomyces roseilus, Diehliomyces microporus, or Mortierella bainieri.

* * * * *